United States Patent [19]

Sih

[11] 4,257,981
[45] Mar. 24, 1981

[54] 2-DECARBOXY-2-AMINOMETHYL-19,20-DIDEHYDRO-PG$_2$ COMPOUNDS

[75] Inventor: John C. Sih, Kalamazoo, Mich.

[73] Assignee: The Upjohn Company, Kalamazoo, Mich.

[21] Appl. No.: 85,627

[22] Filed: Oct. 17, 1979

Related U.S. Application Data

[62] Division of Ser. No. 26,066, Apr. 2, 1979.

[51] Int. Cl.$^3$ .................. C07C 91/02; C07C 91/06; C07C 91/40
[52] U.S. Cl. .................................................. 564/454
[58] Field of Search ............ 260/563 R, 570.9, 573, 260/574, 584 A, 584 R

[56] References Cited

U.S. PATENT DOCUMENTS

| | | | |
|---|---|---|---|
| 3,849,474 | 11/1974 | Abraham et al. | 260/584 A X |
| 3,919,285 | 11/1975 | Axen | 560/121 |
| 3,935,240 | 1/1976 | Mallion | 260/571 X |
| 3,954,741 | 5/1976 | Schaaf et al. | 260/561 R X |
| 4,064,351 | 12/1977 | Sukai et al. | 260/574 |

FOREIGN PATENT DOCUMENTS

2635985 2/1978 Fed. Rep. of Germany ........... 560/121

OTHER PUBLICATIONS

Johnson, "JACS", 100, pp. 7690–7704 (1978).

*Primary Examiner*—John Doll
*Attorney, Agent, or Firm*—Robert A. Armitage

[57] ABSTRACT

The present invention provides novel 2-decarboxy-2-aminomethyl-19,20-didehydro-PG$_2$ compounds, methods for their preparation and pharmacological use for the induction of prostaglandin-like effect.

1 Claim, No Drawings

2-DECARBOXY-2-AMINOMETHYL-19,20-DIDEHYDRO-PG$_2$ COMPOUNDS

Cross Reference to Related Applications

The present application is a division of Ser. No. 26,066, filed Apr. 2, 1979 pending issuance as a U.S. Patent

BACKGROUND OF THE INVENTION

The present invention relates to novel prostaglandin analogs. Particularly, these compounds are analogs of the prostaglandins wherein the C-20—C-19 position is unsaturated, i.e., 19,20-didehydro-PG compounds. Most particularly, the present invention relates to novel 2-decarboxy-2-aminomethyl-19,20-didehydro-PG$_2$ compounds, a disclosure of the preparation and use of which is incorporated here by reference from U.S. Pat. No. 4,228,104.

PRIOR ART

Prostaglandin analogs exhibiting unsaturation in the C-17, C-18, or C-20 position are known in the art. See, for example, U.S. Pat. No. 3,919,285 German Offenlegungsschrift No. 2,635,985 (and its corresponding Derwent Farmdoc CPI No. 10302A), and U.S. Pat. No. 4,064,351 for examples of such compounds. See also the references cited in U.S. Ser. No. 26,066.

SUMMARY OF THE INVENTION

The present invention particularly provides:
A compound of the formula

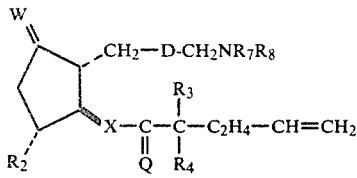

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$)3—CH=CH—,
wherein g is zero one, 2, or 3,
wherein Q is

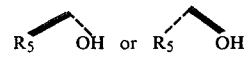

wherein R$_5$ is hydrogen or methyl,
wherein R$_7$ and R$_8$ are
hydrogen, alkyl of one to 12 carbon atoms, inclusive, benzyl, or phenyl, being the same or different. wherein R$_2$ is hydrogen, hydroxyl, or hydroxymethyl; wherein R$_3$ and R$_4$ are hydrogen, methyl, or fluoro, being the same or different, with the proviso that one of R$_3$ and R$_4$ is fluoro only when the other is hydrogen or fluoro;
wherein W is

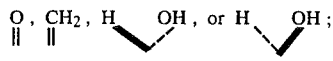

and wherein X is cis— or trans—CH=CH— or —C≡C—.

The compounds of the present invention are particularly useful for inducing prostaglandin-like biological effects, as is described in U.S. Ser. No. 26,066. Uses of compounds in accordance with the present invention include, therefore, anti-asthmatic indication.

I claim:
1. A compound of the formula

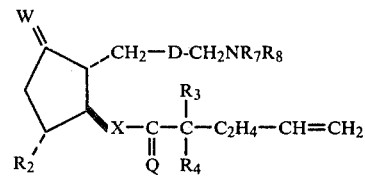

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$) 3—CH=CH—,
wherein g is zero one, 2, or 3,
wherein Q is

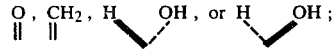

wherein R$_5$ is hydrogen or methyl,
wherein R$_7$ and R$_8$ are
hydrogen, alkyl of one to 12 carbon atoms, inclusive, benzyl, or phenyl, being the same or different.
wherein R$_2$ is hydrogen, hydroxyl, or hydroxymethyl; wherein R$_3$ and R$_4$ are hydrogen, methyl, or fluoro, being the same or different, with the proviso that one of R$_3$ and R$_4$ is fluoro only when the other is hydrogen or fluoro;
wherein W is O, CH$_2$, H OH, or H OH;

and wherein X is cis- or trans—CH=CH— or —C≡C—.

* * * * *

UNITED STATES PATENT OFFICE
CERTIFICATE OF CORRECTION

Patent No. 4,257,981  Dated 24 March 1981

Inventor(s) John C. Sih

It is certified that error appears in the above-identified patent and that said Letters Patent are hereby corrected as shown below:

"Related U.S. Application Data" should read -- Division of Ser. No. 26,066, Apr. 2, 1979, Pat. No. 4,243,611. --

Column 1, lines 7-8, "pending issuance as a U.S. Patent" should read -- now U.S. Patent 4,243,611 --; line 28, "Ser. No. 26,066" should read -- U.S. Patent 4,243,611; lines 49-52, "$R_5 \quad$ OH or $R_5 \quad$ OH" should read -- $R_5 \diagup \diagdown$ OH or $R_5 \diagup \diagdown$ OH --;

Column 2, line 15, "Ser. No. 26,066" should read -- Pat. 4,243,611 --.

Signed and Sealed this

Sixteenth Day of June 1981

[SEAL]

Attest:

RENE D. TEGTMEYER

Attesting Officer  Acting Commissioner of Patents and Trademarks